United States Patent [19]
Nohr et al.

[11] Patent Number: 5,739,175
[45] Date of Patent: Apr. 14, 1998

[54] PHOTOREACTOR COMPOSITION CONTAINING AN ARYLKETOALKENE WAVELENGTH-SPECIFIC SENSITIZER

[75] Inventors: Ronald Sinclair Nohr, Alpharetta; John Gavin MacDonald, Decatur, both of Ga.

[73] Assignee: Kimberly-Clark Worldwide, Inc., Neenah, Wis.

[21] Appl. No.: 463,188

[22] Filed: Jun. 5, 1995

[51] Int. Cl.$^6$ .............................. G03F 7/028; C08F 2/50; C07C 49/794; C07C 69/76
[52] U.S. Cl. .............................. 522/34; 522/42; 522/36; 560/53; 568/335; 568/336
[58] Field of Search .............................. 522/34, 42, 36; 560/53; 568/335, 336

[56] References Cited

U.S. PATENT DOCUMENTS

| | | |
|---|---|---|
| Re. 28,225 | 11/1974 | Heseltine et al. |
| Re. 28,789 | 4/1976 | Chang |
| 575,228 | 1/1897 | von Gallois |
| 582,853 | 5/1897 | Feer |
| 1,013,544 | 1/1912 | Fuerth |
| 1,325,971 | 12/1919 | Akashi |
| 1,364,406 | 1/1921 | Olsen |
| 1,436,856 | 11/1922 | Brenizer et al. |
| 1,744,149 | 1/1930 | Staehlin |
| 1,803,906 | 5/1931 | Krieger et al. |
| 1,876,880 | 9/1932 | Drapal |
| 1,880,572 | 10/1932 | Wendt et al. |
| 1,880,573 | 10/1932 | Wendt et al. |
| 1,916,350 | 7/1933 | Wendt et al. |
| 1,916,779 | 7/1933 | Wendt et al. |
| 1,955,898 | 4/1934 | Wendt et al. |
| 1,962,111 | 6/1934 | Bamberger |
| 2,049,005 | 7/1936 | Gaspar |
| 2,054,390 | 9/1936 | Rust et al. |
| 2,062,304 | 12/1936 | Gaspar |
| 2,097,119 | 10/1937 | Eggert |
| 2,106,539 | 1/1938 | Schnitzspahn |
| 2,111,692 | 3/1938 | Saunders et al. |
| 2,125,015 | 7/1938 | Gaspar |
| 2,130,572 | 9/1938 | Wendt |
| 2,132,154 | 10/1938 | Gaspar |
| 2,145,960 | 2/1939 | Wheatley et al. |
| 2,159,280 | 5/1939 | Mannes et al. |
| 2,171,976 | 9/1939 | Erickson |
| 2,185,153 | 12/1939 | Lecher et al. |
| 2,220,178 | 11/1940 | Schneider |
| 2,230,590 | 2/1941 | Eggert et al. |
| 2,237,885 | 4/1941 | Markush et al. |
| 2,268,324 | 12/1941 | Polgar |

(List continued on next page.)

FOREIGN PATENT DOCUMENTS

| | | |
|---|---|---|
| 103085 | 4/1937 | Australia |
| 12624/88 | 9/1988 | Australia |
| 275245 | 10/1928 | Canada |

(List continued on next page.)

OTHER PUBLICATIONS

Maki, Y. et al., A novel heterocyclic N-oxide, pyrimido[5,4-g]pteridinetetrone 5-oxide, with multifunctional, *Chemical Abstracts*, 122:925 [No. 122:31350 F] 1995.
Abstract of patent, JP 0643573, , : 1994.
Pitchumani, K., "Modification of chemical reactivity upon cyclodextrin encapsulation", *Chemical Abstracts*, 121 : 982 [No. 121:13362 4v] 1994.
Derwent Publications Ltd., London, , , : JP 05297627 (Fujitsu Ltd.), Nov. 12, 1993. (Abstract).
Patent Abstracts of Japan, JP , , : 5241369 (Bando Chem Ind Ltd et al.), Sep. 21, 1993. (Abstract).
Derwent Publications Ltd., London, , , : JP 05232738 (Yamazaki, T.), Sep. 10, 1993. (Abstract).
Derwent Publications Ltd., London, , , : EP 000559310 (Zeneca Ltd.), Sep. 8, 1993. (Abstract).
Derwent Publications Ltd., London, , , : J.A. 5–230410 (Seiko Epson Corp), Sep. 7, 1993. (Abstract).
Derwent Publications Ltd., London, , , : JP 5–230407 (Mitsubishi Kasei Corp), Sep. 7, 1993. (Abstract).
Patent Abstracts of Japan, JP , , : 5197198 (Bando Chem Ind Ltd et al.), Aug. 6, 1993. (Abstract).
Database WPI—Week 9336, Derwent, , : Publications Ltd., London, J.A. 5197069 (Bando Chem), Aug. 6, 1993.
Patent Abstracts of Japan, , , : JP5181308 (Bando Chem Ind Ltd et al.), Jul. 23, 1993. (Abstract).
Patent Abstracts of Japan, JP , , : 5181310 (Bando Chem Ind Ltd et al.), Jul. 23, 1993. (Abstract).
Derwent Publications Ltd., London, , , : JP 5–125318 (Mitsubishi Kasei Corp), May 21, 1993. (Abstract).
Derwent Publications Ltd., London, , , : JP 5–132638 (Mitsubishi Kasei Corp), May 28, 1993. (Abstract).
Abstract of patent, JP 05 117200, , : 1993.
Derwent Publications Ltd., London, , , : JP 05061246 (Ricoh KK), Mar. 12, 1993. (Abstract).
Husain, N. et al., "Cyclodextrins as mobile–phase additives in reversed–phase HPLC", *American Laboratory*, 82:80–87, 1993.
Hamilton, D.P., "Tired of Shredding? New Ricoh Method Tries Different Tack", *Wall Street Journal*, :B2, 1993.
Duxbury, "The Photochemistry and Photophysics of Triphenylmethane Dyes in Solid Liquid Media", *Chemical Review*, 93:381–433, 1993.
Abstract of patent, JP 04351603, , : 1992.
Abstract of patent, JP 04351602, , : 1992.
Derwent Publications Ltd., London, , , : JP 4–314769 (Citizen Watch Co Ltd), Nov. 5, 1992. (Abstract).
Abstract of patent, JP 04315739, , : 1992.

(List continued on next page.)

*Primary Examiner*—Susan S. Berman
*Attorney, Agent, or Firm*—Jones & Askew

[57] ABSTRACT

A method of generating reactive species which includes exposing a photoreactor composition to radiation, in which the photoreactor composition comprises a wavelength-specific sensitizer associated with a reactive species-generating photoinitiator. Also described are methods of polymerizing unsaturated monomers and curing an unsaturated oligomer/monomer mixture.

3 Claims, 1 Drawing Sheet

U.S. PATENT DOCUMENTS

| | | |
|---|---|---|
| 2,281,895 | 5/1942 | van Poser et al. . |
| 2,328,166 | 8/1943 | Poigar et al. . |
| 2,346,090 | 4/1944 | Staehle . |
| 2,349,090 | 5/1944 | Haddock . |
| 2,356,618 | 8/1944 | Rossander et al. . |
| 2,361,301 | 10/1944 | Libby, Jr. et al. . |
| 2,364,359 | 12/1944 | Kienle et al. . |
| 2,381,145 | 8/1945 | von Glahn et al. . |
| 2,382,904 | 8/1945 | Federsen . |
| 2,386,646 | 10/1945 | Adams et al. . |
| 2,402,106 | 6/1946 | von Glahn et al. . |
| 2,416,145 | 2/1947 | Biro . |
| 2,477,165 | 7/1949 | Bergstrom . |
| 2,527,347 | 10/1950 | Bergstrom . |
| 2,601,669 | 6/1952 | Tullsen . |
| 2,612,494 | 9/1952 | von Glahn et al. . |
| 2,612,495 | 9/1952 | von Glahn et al. . |
| 2,628,959 | 2/1953 | von Glahn et al. . |
| 2,728,784 | 12/1955 | Tholstrup et al. . |
| 2,732,301 | 1/1956 | Robertson et al. ............ 522/34 |
| 2,744,103 | 5/1956 | Koch . |
| 2,757,090 | 7/1956 | Meugebauer et al. . |
| 2,763,550 | 9/1956 | Lovick . |
| 2,768,171 | 10/1956 | Clarke et al. . |
| 2,773,056 | 12/1956 | Helfaer . |
| 2,798,000 | 7/1957 | Monterman . |
| 2,809,189 | 10/1957 | Stanley et al. . |
| 2,834,773 | 5/1958 | Scalera et al. . |
| 2,897,187 | 7/1959 | Koch . |
| 2,936,241 | 5/1960 | Sharp et al. . |
| 2,940,853 | 6/1960 | Sagura et al. ............... 522/34 |
| 2,992,198 | 7/1961 | Funahashi . |
| 3,030,208 | 4/1962 | Schellenberg et al. . |
| 3,071,815 | 1/1963 | MacKinnon . |
| 3,104,973 | 9/1963 | Sprague et al. . |
| 3,114,634 | 12/1963 | Brown et al. . |
| 3,121,632 | 2/1964 | Sprague et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiesbaden . |
| 3,178,285 | 4/1965 | Anderau et al. . |
| 3,242,215 | 3/1966 | Heitmiller . |
| 3,284,205 | 11/1966 | Sprague et al. . |
| 3,300,314 | 1/1967 | Rauner et al. . |
| 3,304,297 | 2/1967 | Wegmann et al. . |
| 3,305,361 | 2/1967 | Gaynor et al. . |
| 3,313,797 | 4/1967 | Kissa . |
| 3,359,109 | 12/1967 | Harder et al. . |
| 3,361,827 | 1/1968 | Biletch . |
| 3,385,700 | 5/1968 | Willems et al. . |
| 3,397,984 | 8/1968 | Williams et al. . |
| 3,418,118 | 12/1968 | Thommes et al. . |
| 3,479,185 | 11/1969 | Chambers . |
| 3,502,476 | 3/1970 | Kohei et al. . |
| 3,503,744 | 3/1970 | Itano et al. . |
| 3,514,597 | 5/1970 | Haes et al. . |
| 3,547,646 | 12/1970 | Hori et al. . |
| 3,563,931 | 2/1971 | Horiguchi . |
| 3,574,624 | 4/1971 | Reynolds et al. . |
| 3,595,655 | 7/1971 | Robinson et al. . |
| 3,595,657 | 7/1971 | Robinson et al. . |
| 3,595,658 | 7/1971 | Gerlach et al. . |
| 3,595,659 | 7/1971 | Gerlach et al. . |
| 3,607,639 | 9/1971 | Krefeld et al. . |
| 3,607,693 | 9/1971 | Heine et al. . |
| 3,607,863 | 9/1971 | Dosch . |
| 3,615,562 | 10/1971 | Harrison et al. . |
| 3,617,288 | 11/1971 | Hartman ................ 522/34 |
| 3,637,337 | 1/1972 | Pilling . |
| 3,637,581 | 1/1972 | Horioguchi et al. . |
| 3,642,472 | 2/1972 | Mayo . |
| 3,647,467 | 3/1972 | Grubb . |
| 3,667,954 | 6/1972 | Itano et al. . |
| 3,668,188 | 6/1972 | King et al. . |
| 3,669,925 | 6/1972 | King et al. . |
| 3,671,096 | 6/1972 | Mackin . |
| 3,671,251 | 6/1972 | Houle et al. . |
| 3,676,690 | 7/1972 | McMillin et al. . |
| 3,678,044 | 7/1972 | Adams . |
| 3,695,879 | 10/1972 | Laming et al. . |
| 3,697,280 | 10/1972 | Strilko . |
| 3,707,371 | 12/1972 | Files . |
| 3,729,313 | 4/1973 | Smith . |
| 3,737,628 | 6/1973 | Azure . |
| 3,765,896 | 10/1973 | Fox . |
| 3,775,130 | 11/1973 | Enomoto et al. . |
| 3,788,849 | 1/1974 | Taguchi et al. . |
| 3,799,773 | 3/1974 | Watarai et al. . |
| 3,800,439 | 4/1974 | Sokolski et al. . |
| 3,817,752 | 6/1974 | Laridon et al. . |
| 3,840,338 | 10/1974 | Zviak et al. . |
| 3,870,524 | 3/1975 | Watanabe et al. ............ 96/115 P |
| 3,873,500 | 3/1975 | Kato et al. . |
| 3,887,450 | 6/1975 | Gilano et al. . |
| 3,895,949 | 7/1975 | Akamatsu . |
| 3,914,166 | 10/1975 | Rudolph et al. . |
| 3,915,824 | 10/1975 | McGinniss . |
| 3,919,323 | 11/1975 | Houlihan et al. . |
| 3,978,132 | 8/1976 | Houlihan et al. . |
| 3,984,248 | 10/1976 | Sturmer . |
| 3,988,154 | 10/1976 | Sturmer . |
| 4,012,256 | 3/1977 | Levinos . |
| 4,043,819 | 8/1977 | Baumann . |
| 4,048,034 | 9/1977 | Martan . |
| 4,056,665 | 11/1977 | Tayler et al. . |
| 4,058,400 | 11/1977 | Crivello . |
| 4,067,892 | 1/1978 | Thorne et al. . |
| 4,073,968 | 2/1978 | Miyamoto et al. . |
| 4,079,183 | 3/1978 | Green . |
| 4,090,877 | 5/1978 | Streeper . |
| 4,100,047 | 7/1978 | McCarty . |
| 4,107,733 | 8/1978 | Schickedanz . |
| 4,110,112 | 8/1978 | Roman et al. . |
| 4,111,699 | 9/1978 | Krueger . |
| 4,114,028 | 9/1978 | Baio et al. . |
| 4,148,658 | 4/1979 | Kondoh et al. . |
| 4,162,162 | 7/1979 | Dueber . |
| 4,171,977 | 10/1979 | Hasegawa et al. ............ 96/115 P |
| 4,179,577 | 12/1979 | Green . |
| 4,181,807 | 1/1980 | Green . |
| 4,229,172 | 10/1980 | Baumann et al. . |
| 4,232,106 | 11/1980 | Iwasaki et al. . |
| 4,239,843 | 12/1980 | Hara et al. . |
| 4,239,850 | 12/1980 | Kita et al. ............... 430/281 |
| 4,241,155 | 12/1980 | Hara et al. . |
| 4,242,430 | 12/1980 | Hara et al. . |
| 4,242,431 | 12/1980 | Hara et al. . |
| 4,245,018 | 1/1981 | Hara et al. . |
| 4,245,995 | 1/1981 | Hugl et al. . |
| 4,246,330 | 1/1981 | Hara et al. . |
| 4,248,949 | 2/1981 | Hara et al. . |
| 4,250,096 | 2/1981 | Kvita et al. . |
| 4,251,622 | 2/1981 | Kimoto et al. . |
| 4,254,195 | 3/1981 | Hara et al. . |
| 4,256,493 | 3/1981 | Yokoyama et al. . |
| 4,256,817 | 3/1981 | Hara et al. . |
| 4,258,123 | 3/1981 | Nagashima et al. ............ 430/281 |
| 4,259,432 | 3/1981 | Kondoh et al. . |
| 4,262,936 | 4/1981 | Miyamoto . |
| 4,268,605 | 5/1981 | Hara et al. . |

| Patent No. | Date | Name |
|---|---|---|
| 4,268,667 | 5/1981 | Anderson . |
| 4,269,926 | 5/1981 | Hara et al. . |
| 4,270,130 | 5/1981 | Houle et al. . |
| 4,271,252 | 6/1981 | Hara et al. . |
| 4,271,253 | 6/1981 | Hara et al. . |
| 4,272,244 | 6/1981 | Schlick . |
| 4,279,982 | 7/1981 | Iwasaki et al. . |
| 4,279,985 | 7/1981 | Nonogaki et al. . |
| 4,284,485 | 8/1981 | Berner . |
| 4,289,844 | 9/1981 | Specht et al. . |
| 4,290,870 | 9/1981 | Kondoh et al. . |
| 4,298,679 | 11/1981 | Shinozaki et al. ............... 522/34 |
| 4,300,123 | 11/1981 | McMillin et al. . |
| 4,306,014 | 12/1981 | Kunikane et al. . |
| 4,307,182 | 12/1981 | Dalzell et al. . |
| 4,308,400 | 12/1981 | Felder et al. . |
| 4,315,807 | 2/1982 | Felder et al. . |
| 4,318,705 | 3/1982 | Nowak et al. . |
| 4,318,791 | 3/1982 | Felder et al. . |
| 4,335,054 | 6/1982 | Blaser et al. . |
| 4,335,055 | 6/1982 | Blaser et al. . |
| 4,336,323 | 6/1982 | Winslow . |
| 4,343,891 | 8/1982 | Aasen et al. . |
| 4,345,011 | 8/1982 | Drexhage . |
| 4,347,111 | 8/1982 | Gehlhaus et al. . |
| 4,349,617 | 9/1982 | Kawashiri et al. . |
| 4,350,753 | 9/1982 | Shelnut et al. . |
| 4,351,893 | 9/1982 | Anderson . |
| 4,356,255 | 10/1982 | Tachikawa et al. . |
| 4,359,524 | 11/1982 | Masuda et al. . |
| 4,362,806 | 12/1982 | Whitmore . |
| 4,367,072 | 1/1983 | Vogtle et al. . |
| 4,367,280 | 1/1983 | Kondo et al. . |
| 4,369,283 | 1/1983 | Altschuler . |
| 4,370,401 | 1/1983 | Winslow et al. . |
| 4,373,020 | 2/1983 | Winslow . |
| 4,376,887 | 3/1983 | Greenaway et al. . |
| 4,390,616 | 6/1983 | Sato et al. . |
| 4,391,867 | 7/1983 | Derick et al. . |
| 4,399,209 | 8/1983 | Sanders et al. . |
| 4,416,961 | 11/1983 | Drexhage . |
| 4,424,325 | 1/1984 | Tsunoda et al. . |
| 4,425,162 | 1/1984 | Sugiyama et al. . |
| 4,425,424 | 1/1984 | Altland et al. . |
| 4,434,035 | 2/1984 | Eichler et al. . |
| 4,447,521 | 5/1984 | Tiers et al. . |
| 4,450,227 | 5/1984 | Holmes et al. . |
| 4,460,676 | 7/1984 | Fabel . |
| 4,467,112 | 8/1984 | Matsuura et al. . |
| 4,475,999 | 10/1984 | Via . |
| 4,496,447 | 1/1985 | Eichler et al. . |
| 4,510,392 | 4/1985 | Litt et al. . |
| 4,523,924 | 6/1985 | Lacroix . |
| 4,524,122 | 6/1985 | Weber et al. . |
| 4,548,896 | 10/1985 | Sabongi et al. . |
| 4,555,474 | 11/1985 | Kawamura . |
| 4,565,769 | 1/1986 | Dueber et al. . |
| 4,567,171 | 1/1986 | Mangum . |
| 4,571,377 | 2/1986 | McGinniss et al. . |
| 4,595,745 | 6/1986 | Nakano et al. . |
| 4,604,344 | 8/1986 | Irving et al. . |
| 4,613,334 | 9/1986 | Thomas et al. . |
| 4,617,380 | 10/1986 | Hinson et al. . |
| 4,622,286 | 11/1986 | Sheets . |
| 4,632,891 | 12/1986 | Banks et al. . |
| 4,632,895 | 12/1986 | Patel et al. . |
| 4,634,644 | 1/1987 | Irving et al. . |
| 4,638,340 | 1/1987 | Iiyama et al. . |
| 4,663,275 | 5/1987 | West et al. . |
| 4,663,641 | 5/1987 | Iiyama et al. . |
| 4,668,533 | 5/1987 | Miller . |
| 4,672,041 | 6/1987 | Jain . |
| 4,698,291 | 10/1987 | Koibuchi et al. . |
| 4,701,402 | 10/1987 | Patel et al. . |
| 4,702,996 | 10/1987 | Griffing et al. . |
| 4,707,161 | 11/1987 | Thomas et al. . |
| 4,707,425 | 11/1987 | Sasagawa et al. . |
| 4,707,430 | 11/1987 | Ozawa et al. . |
| 4,720,450 | 1/1988 | Ellis . |
| 4,721,734 | 1/1988 | Gehlhaus et al. . |
| 4,724,021 | 2/1988 | Martin et al. . |
| 4,724,201 | 2/1988 | Okazaki et al. . |
| 4,725,527 | 2/1988 | Robillard . |
| 4,737,438 | 4/1988 | Ito et al. . |
| 4,740,451 | 4/1988 | Kohara . |
| 4,745,042 | 5/1988 | Sasago et al. . |
| 4,755,450 | 7/1988 | Sanders et al. . |
| 4,761,181 | 8/1988 | Suzuki . |
| 4,766,050 | 8/1988 | Jerry . |
| 4,766,055 | 8/1988 | Kawabata et al. . |
| 4,771,802 | 9/1988 | Tannenbaum . |
| 4,772,291 | 9/1988 | Shibanai et al. . |
| 4,772,541 | 9/1988 | Gottschalk . |
| 4,775,386 | 10/1988 | Reinert et al. . |
| 4,786,586 | 11/1988 | Lee et al. . |
| 4,800,149 | 1/1989 | Gottschalk . |
| 4,808,189 | 2/1989 | Oishi et al. . |
| 4,812,139 | 3/1989 | Brodmann . |
| 4,812,517 | 3/1989 | West . |
| 4,813,970 | 3/1989 | Kirjanov et al. . |
| 4,822,714 | 4/1989 | Sanders . |
| 4,837,106 | 6/1989 | Ishikawa et al. . |
| 4,837,331 | 6/1989 | Yamanishi et al. . |
| 4,838,938 | 6/1989 | Tomida et al. . |
| 4,839,269 | 6/1989 | Okazaki et al. . |
| 4,849,320 | 7/1989 | Irving et al. . |
| 4,853,395 | 8/1989 | Carr et al. . |
| 4,853,398 | 8/1989 | Carr et al. . |
| 4,857,438 | 8/1989 | Loerzer et al. . |
| 4,861,916 | 8/1989 | Kohler et al. . |
| 4,865,942 | 9/1989 | Gottschalk et al. . |
| 4,874,391 | 10/1989 | Reinert . |
| 4,895,880 | 1/1990 | Gottschalk . |
| 4,900,581 | 2/1990 | Stuke et al. . |
| 4,902,299 | 2/1990 | Anton . |
| 4,902,725 | 2/1990 | Moore . |
| 4,902,787 | 2/1990 | Freeman . |
| 4,925,770 | 5/1990 | Ichiura et al. . |
| 4,933,948 | 6/1990 | Herkstroeter . |
| 4,937,161 | 6/1990 | Kita et al. . |
| 4,942,113 | 7/1990 | Trundle . |
| 4,952,680 | 8/1990 | Schmeidl . |
| 4,954,380 | 9/1990 | Kanome et al. . |
| 4,956,254 | 9/1990 | Washizu et al. . |
| 4,968,813 | 11/1990 | Rule et al. . |
| 4,985,345 | 1/1991 | Hayakawa et al. . |
| 4,987,056 | 1/1991 | Imahashi et al. . |
| 4,997,745 | 3/1991 | Kawamura et al. . |
| 5,001,330 | 3/1991 | Koch . |
| 5,002,853 | 3/1991 | Aoai et al. . |
| 5,002,993 | 3/1991 | West et al. . |
| 5,003,142 | 3/1991 | Fuller . |
| 5,006,758 | 4/1991 | Gellert et al. . |
| 5,013,959 | 5/1991 | Kogelschatz . |
| 5,023,129 | 6/1991 | Morganti et al. . |
| 5,025,036 | 6/1991 | Carson et al. . |
| 5,026,427 | 6/1991 | Mitchell et al. . |
| 5,028,792 | 7/1991 | Mullis . |
| 5,034,526 | 7/1991 | Bonham et al. . |
| 5,045,435 | 9/1991 | Adams et al. . |
| 5,045,573 | 9/1991 | Kohler et al. . |
| 5,053,320 | 10/1991 | Robbillard . |
| 5,055,579 | 10/1991 | Pawlowski et al. . |
| 5,070,001 | 12/1991 | Stahlhofen . |

| | | | | | | |
|---|---|---|---|---|---|---|
| 5,076,808 | 12/1991 | Hahn et al. | | 5,312,713 | 5/1994 | Yokoyama et al. |
| 5,085,698 | 2/1992 | Ma et al. | | 5,312,721 | 5/1994 | Gesign. |
| 5,087,550 | 2/1992 | Blum et al. | | 5,324,349 | 6/1994 | Sano et al. |
| 5,089,374 | 2/1992 | Saeva. | | 5,328,504 | 7/1994 | Ohnishi. |
| 5,096,489 | 3/1992 | Laver. | | 5,330,860 | 7/1994 | Grot et al. |
| 5,098,806 | 3/1992 | Robillard. | | 5,334,455 | 8/1994 | Noren et al. |
| 5,106,723 | 4/1992 | West et al. | | 5,340,631 | 8/1994 | Matsuzawa et al. |
| 5,108,505 | 4/1992 | Moffat. | | 5,340,854 | 8/1994 | Martic et al. |
| 5,108,874 | 4/1992 | Griffing et al. | | 5,356,464 | 10/1994 | Hickman et al. |
| 5,110,706 | 5/1992 | Yumoto et al. | | 5,362,592 | 11/1994 | Murofushi et al. |
| 5,110,709 | 5/1992 | Aoai et al. | | 5,372,917 | 12/1994 | Tsuchida et al. |
| 5,114,832 | 5/1992 | Zertani et al. | | 5,376,503 | 12/1994 | Audett et al. |
| 5,124,723 | 6/1992 | Laver. | | 5,393,580 | 2/1995 | Ma et al. |
| 5,130,227 | 7/1992 | Wade et al. | | 5,401,303 | 3/1995 | Stoffel et al. |
| 5,133,803 | 7/1992 | Moffatt. | | 5,415,976 | 5/1995 | Zaki. |
| 5,135,940 | 8/1992 | Belander et al. | | 5,426,164 | 6/1995 | Babb et al. |
| 5,139,572 | 8/1992 | Kawashima. | | 5,455,143 | 10/1995 | Ali .................................... 522/34 |
| 5,141,556 | 8/1992 | Matrick. | | | | |
| 5,141,797 | 8/1992 | Wheeler. | | FOREIGN PATENT DOCUMENTS | | |
| 5,147,901 | 9/1992 | Rutsch et al. | | 413257 | 1/1935 | Canada. |
| 5,153,104 | 10/1992 | Rossman et al. | | 458808 | 12/1936 | Canada. |
| 5,153,105 | 10/1992 | Sher et al. | | 460268 | 10/1949 | Canada. |
| 5,153,166 | 10/1992 | Jain et al. | | 461082 | 11/1949 | Canada. |
| 5,160,372 | 11/1992 | Matrick. | | 463021 | 2/1950 | Canada. |
| 5,166,041 | 11/1992 | Murofushi et al. | | 463022 | 2/1950 | Canada. |
| 5,169,436 | 12/1992 | Matrick. | | 465495 | 5/1950 | Canada. |
| 5,169,438 | 12/1992 | Matrick. | | 465496 | 5/1950 | Canada. |
| 5,173,112 | 12/1992 | Matrick et al. | | 465499 | 5/1950 | Canada. |
| 5,176,984 | 1/1993 | Hipps, Sr. et al. | | 483214 | 5/1952 | Canada. |
| 5,178,420 | 1/1993 | Shelby. | | 517364 | 10/1955 | Canada. |
| 5,180,425 | 1/1993 | Matrick et al. | | 537687 | 3/1957 | Canada. |
| 5,180,652 | 1/1993 | Yamaguchi et al. | | 552565 | 2/1958 | Canada. |
| 5,185,236 | 2/1993 | Shiba et al. | | 779239 | 2/1968 | Canada. |
| 5,187,045 | 2/1993 | Bonham et al. | | 930103 | 7/1973 | Canada. |
| 5,187,049 | 2/1993 | Sher et al. | | 2053094 | 4/1992 | Canada. |
| 5,190,565 | 3/1993 | Berenbaum et al. | | 94118 | 5/1958 | Czechoslovakia. |
| 5,190,845 | 3/1993 | Hashimoto et al. | | 0223587 | 5/1987 | European Pat. Off. |
| 5,196,295 | 3/1993 | Davis. | | 0280458 | 8/1988 | European Pat. Off. |
| 5,198,330 | 3/1993 | Martic et al. | | 0308274 | 3/1989 | European Pat. Off. |
| 5,202,209 | 4/1993 | Winnik et al. | | 0375160 | 6/1990 | European Pat. Off. |
| 5,202,210 | 4/1993 | Matsuoka et al. | | 0390439 | 10/1990 | European Pat. Off. |
| 5,202,211 | 4/1993 | Vercoulen. | | 0468465 | 1/1992 | European Pat. Off. |
| 5,202,212 | 4/1993 | Shin et al. | | 0542286 | 5/1993 | European Pat. Off. |
| 5,202,213 | 4/1993 | Nakahara et al. | | 000571190 | 11/1993 | European Pat. Off. |
| 5,202,215 | 4/1993 | Kanakura et al. | | 1039835 | 9/1958 | Germany. |
| 5,202,221 | 4/1993 | Imai et al. | | 1047013 | 12/1958 | Germany. |
| 5,205,861 | 4/1993 | Matrick. | | 1132450 | 7/1962 | Germany. |
| 5,208,136 | 5/1993 | Zanoni et al. | | 244520 | 3/1975 | Germany. |
| 5,209,814 | 5/1993 | Felten et al. | | 2714978 | 10/1977 | Germany. |
| 5,219,703 | 6/1993 | Bugner et al. | | 3415033 | 10/1984 | Germany. |
| 5,221,334 | 6/1993 | Ma et al. | | 2146357 | 4/1985 | Germany. |
| 5,224,197 | 6/1993 | Zanoni et al. | | 3833437 | 4/1990 | Germany. |
| 5,224,476 | 7/1993 | Schultz et al. | | 3833438 | 4/1990 | Germany. |
| 5,224,987 | 7/1993 | Matrick. | | 004036328 | 7/1991 | Germany. |
| 5,241,059 | 8/1993 | Yoshinaga. | | 50-65592 | 6/1975 | Japan. |
| 5,250,109 | 10/1993 | Chan et al. | | 0014233 | 2/1981 | Japan. |
| 5,258,274 | 11/1993 | Helland et al. | | 56-14569 | 2/1981 | Japan. |
| 5,262,276 | 11/1993 | Kawamura. | | 56-36556 | 4/1981 | Japan. |
| 5,268,027 | 12/1993 | Chan et al. | | 58-211426 | 12/1983 | Japan. |
| 5,270,078 | 12/1993 | Walker et al. | | 59-219270 | 4/1985 | Japan. |
| 5,271,765 | 12/1993 | Ma. | | 60-239739 | 11/1985 | Japan. |
| 5,272,201 | 12/1993 | Ma et al. | | 60-239740 | 11/1985 | Japan. |
| 5,275,646 | 1/1994 | Marshall et al. | | 60-239741 | 11/1985 | Japan. |
| 5,279,652 | 1/1994 | Kaufmann et al. | | 60-239743 | 11/1985 | Japan. |
| 5,284,734 | 2/1994 | Blum et al. | | 61-3781 | 1/1986 | Japan. |
| 5,294,528 | 3/1994 | Furutachi. | | 62-7703 | 1/1987 | Japan. |
| 5,296,275 | 3/1994 | Goman et al. | | 62-100557 | 5/1987 | Japan. |
| 5,296,556 | 3/1994 | Frihart. | | 62-127281 | 6/1987 | Japan. |
| 5,300,403 | 4/1994 | Angelopolus et al. | | 63-43959 | 2/1988 | Japan. |
| 5,302,195 | 4/1994 | Helbrecht. | | 63-223077 | 9/1988 | Japan. |
| 5,302,197 | 4/1994 | Wickramanayke et al. | | 63-223078 | 9/1988 | Japan. |
| 5,310,778 | 5/1994 | Shor et al. | | 6429337 | 1/1989 | Japan. |

| | | |
|---|---|---|
| 64-40948 | 2/1989 | Japan . |
| 89014948 | 3/1989 | Japan . |
| 1146974 | 6/1989 | Japan . |
| 01210477 | 8/1989 | Japan . |
| 292957 | 4/1990 | Japan . |
| 2179642 | 7/1990 | Japan . |
| 2282261 | 11/1990 | Japan . |
| 03163566 | 7/1991 | Japan . |
| 5134447 | 11/1991 | Japan . |
| 3284668 | 12/1991 | Japan . |
| 4023884 | 1/1992 | Japan . |
| 4023885 | 1/1992 | Japan . |
| 4-136075 | 5/1992 | Japan . |
| 561220 | 3/1993 | Japan . |
| 5-140498 | 6/1993 | Japan . |
| 5263067 | 10/1993 | Japan . |
| 6214339 | 8/1994 | Japan . |
| 6256494 | 9/1994 | Japan . |
| 6256633 | 9/1994 | Japan . |
| 1310767 | 5/1987 | U.S.S.R. . |
| 349339 | 5/1931 | United Kingdom . |
| 355686 | 8/1931 | United Kingdom . |
| 399753 | 10/1933 | United Kingdom . |
| 441085 | 1/1936 | United Kingdom . |
| 463515 | 4/1937 | United Kingdom . |
| 492711 | 9/1938 | United Kingdom . |
| 518612 | 3/1940 | United Kingdom . |
| 539912 | 9/1941 | United Kingdom . |
| 626727 | 7/1947 | United Kingdom . |
| 600451 | 4/1948 | United Kingdom . |
| 616362 | 1/1949 | United Kingdom . |
| 618616 | 2/1949 | United Kingdom . |
| 779389 | 7/1957 | United Kingdom . |
| 1372884 | 11/1974 | United Kingdom . |
| 9211295 | 7/1992 | WIPO . |
| 93/06597 | 4/1993 | WIPO . |
| 94/22500 | 10/1994 | WIPO . |
| 94/22501 | 10/1994 | WIPO . |

OTHER PUBLICATIONS

Derwent Publications Ltd., London, , , : JP 04300395 (Funai Denki KK), Oct. 23, 1992. (Abstract).

Derwent Publications Ltd., London, , , :JP 4–213374 (Mitsubishi Kasei Corp), Aug. 4, 1992. (Abstract).

Abstract of patent, JP 04210228, , : 1992.

Derwent Publications Ltd., London, , , : J.P. 4–202271 (Mitsubishi Kasei Corp), Jul. 23, 1992. (Abstract).

Derwent Publications Ltd., London, , , : J.A. 4–202571 (Canon Inc.), Jul. 23, 1992. (Abstract).

Derwent Publications Ltd., London, , , : JP 4–189877 (Seiko Epson Corp), Jul. 8, 1992. (Abstract).

Derwent Publications Ltd., London, , , : JP 4–189876 (Seiko Epson Corp), Jul. 8, 1992. (Abstract).

Derwent Publications Ltd., London, , , : J.A. 4–170479 (Seiko Epson Corp), Jun. 18, 1992. (Abstract).

Abstract of patent, JP 0481402, , : 1992.

Abstract of patent, JP 0481401, , : 1992.

Derwent Publications Ltd., London, . . . : J0 3247676 (Canon KK), Nov. 5, 1991. (Abstract).

Abstract of patent, JP 03–220384, , : 1991.

Derwent Publications Ltd., London, , , : JP 3167270 (Misubishi Kasei Corp), Jul. 19, 1991. (Abstract).

Derwent Publications Ltd., London, , , : J0 3093870 (Dainippon Ink Chem KK), Apr. 18, 1991. (Abstract).

Abstract of patent, JP 06369890, , : 1991.

Abstract of patent, JP 03 41165, , : 1991.

"Cloring/Decoloring Agent for Tonor Use Developed" *Japan Chemical Week,* 1991.

Braithwaite, M. et al., "Formulation", *Chemistry & Technology of UV & EB Formulation for Coatings, Inks & Paints,* IV : 11–12 1991.

*Scientific Polymer Products, Inc. Brochure,* : 24–31, 1991.

Dietliker, K., "Photoiniators for Free Radical and Catioinc Polymerisation", *Chemistry & Technology of UV & EB Formulation for Coatings, Inks & Paints,* III : 1991.

Abstract of patent, JP 02289652, , : 1990.

Abstract of Patent, JP 0297957, , , : (Fuji Xerox Co., Ltd.), 1990.

Derwent Publications Ltd., London, , , : JP 2091166 (Canon KK), Mar. 30, 1990. (Abstract).

Kogelschatz, U., "Silent Discharges for the Generation of ultraviolet and vacuum ultraviolet excimer radiation", *Pure & Applied Chem.,* 62 : 1667–74, 1990.

Abstract of patent, JP 01299083, , : 1989.

Derwent Publications Ltd., London, , , : J.0 1182379 (Canon KK), Jul. 20, 1989. (Abstract).

Derwent Publications Ltd., London, , , : J.0, 1011171 (Mitsubishi Chem Ind KK), Jan. 13, 1989. (Abstract).

"Xerographic Materials", *Encyclopedia of Polymer Science and Engineering,* 17 : 918–943 1989.

Pappas, S.P., "Photocrosslinking", *Comph. Pol. Sci.,* 6 : 135–148, 1989.

Pappas, S.P., "Photoinitiated Polymerization", *Comph. Pol. Sci.,* 4 : 337–355, 1989.

Kirilenko, G.V., "An analog of the vesicular process with amplitude modulation of the incident light beam", *Chemical Abstracts,* 111 : 569 [No. 111:12363 3b], 1989.

Abstract of patent, JP 63190815, , : 1988.

Abstract of patent, JP 63144329, , : 1988.

Abstract of patent, JP 63130164, , : 1988.

Abstract of patent, JP 6177846, , : 1988.

Abstract of patent, JP 6373241, , : 1988.

Abstract of patent, JP 6347762, , , : 1988.

Abstract of patent, JP 63 47763, , , : 1988.

Abstract of patent, JP 63–47764, , , : 1988.

Abstract of patent, JP 63–47765, , , : 1988.

Eliasson, B., et al., "UV Excimer Radiation from Dielectric–Barrier Discharges", *Applied Physics B,* 46 : 299–303, 1988.

Abstract of patent, JP 62215261, , : 1987.

Abstract of patent, JP 6232082, , : 1987.

Derwent Publications Ltd., London, , , : J6 2007772 (Alps Electric KK), Jan. 14, 1987. (Abstract).

Derwent Publications Ltd., London, , , : JA 0284478 (Sanyo Chem Ind Ltd), Dec. 15, 1986. (Abstract).

Abstract of patent, JP 61251842, , : 1986.

Abstract of patent, JP 6197025, , : 1986.

Abstract of patent, JP 6187760, , : 1986.

Derwent Publications Ltd., London, , , : DL 0234731 (Karl Marx Univ. Leipzig), Apr. 9, 1986. (Abstract).

Derwent Publications Ltd., London, , , : J. 0226575 (Sumitomo Chem Ind KK), Oct. 11, 1985. (Abstract).

Abstract of patent, JP 60156761, , : 1985.

Derwent Publications Ltd., London, , , : J.A. 0011451 (Fugi Photo Film KK), Jan. 21, 1985. (Abstract).

Roos, G. et al., "Textile applications of photocrosslinkable polymers", *Chemical Abstracts,* 103: 57 [No. 103 :23690j], 1985.

Derwent Publications Ltd., London, , , : JP 0198187 (Canon KK), Nov. 9, 1984. (Abstract).

Derwent Publications Ltd., London, , , : J.A. 0169883 (Ricoh KK), Sep. 25, 1984. (Abstract).

Derwent Publications Ltd., London, , , : J,A, 0053563 (Dainippon Toryo KK), Mar. 28, 1984. (Abstract).

Saenger, W., "Structural Aspects of Cyclodextrins and Their Inclusion Complexes", *Inclusion Compounds—Structural Aspects of Inclusion Compounds*, 2 : 231–259, 1984.

Szejtli, "Industrial Applications of Cyclodextrins", Inclusion Compounds: Physical Prop. & Applns, 3 : 331–390, 1984.

"Clathrate Compounds, Molecular Inclusion Phenomena, and Cyclodextrins", *D. Reidel Publishing*, : 714–746, 1984.

van Beek, H.C.A, "Light–Induced Colour Changes in Dyes and Materials", *Color Res. and Appl.*, 8 : 176–181, 1983.

Connors, K.A., "Application of a stoichiometric model of cyclodextrin complex formation", *Chemical Abstracts*, 98 : 598 [No. 98 :53067g], 1983.

Derwent Publications Ltd., London, . . : EP 0065617 (IBM Corp.), Dec. 1, 1982, (Abstract).

Derwent Publications Ltd., London, , , : J,A, 0187289 (Honshu Paper Mfg KK), Nov. 17, 1982. (Abstract).

Derwent Publications Ltd., London, . . : JA 0185364 (Ricoh KK), Nov. 15, 1982. (Abtract).

Derwent Publications Ltd., London, , , : J,A, 0090069 (Canon KK), Jun. 4, 1982. (Abstract).

Derwent Publications Ltd., London, , , : J,A, 0010661 (Canon KK), Jan. 20, 1982. (Abstract).

Derwent Publications Ltd., London, , , : J,A, 0010659 (Canon KK), Jan. 20, 1982. (Abstract).

Derwent Publications Ltd., London, , , : J,A, 0155263 (Canon KK), Dec. 1, 1981. (Abstract).

Derwent Publications Ltd., London, , , : J,A, 0147861 (Canon KK), Nov. 17, 1981. (Abstract).

Derwent Publications Ltd., London, , , : J,A, 0143273 (Canon KK), Nov. 7, 1981. (Abstract).

Derwent Publications Ltd., London, , , : J,A, 0136861 (Canon KK), Oct. 26, 1981. (Abstract).

Derwent Publications Ltd., London, , , : J,A, 6133378 (Canon KK), Oct. 19, 1981. (Abstract).

Derwent Publications Ltd., London, , , : J,A, 6133377 (Canon KK), Oct. 19, 1981. (Abstract).

Derwent Publications Ltd., London, , , : J,A, 6093775 (Canon KK), Jul. 29, 1981. (Abstract).

Derwent Publications Ltd., London, , , : J,A, 0008135 (Ricoh KK), Jan. 27, 1981. (Abstract).

Derwent Publications Ltd., London, , , : J,A, 0004488 (Canon KK), Jan. 17, 1981. (Abstract).

Rosanske et al., "Stoichiometric Model of Cyclodextrin Complex Formation", *Journal of Pharmaceutical Sciences*, 69 :564–567 (5), 1980.

Derwent Publications Ltd., London, . . : J,A, 0005422 (Fuji Photo Film KK), Jan. 16, 1979. (Abstract).

"Color imaging devices and color filter arrays using photo–bleachable dyes", *Research Disclosure*, : 22–23 1979.

"Electrophotography", *Kirk–Othmer Encyclopedia of Chemical Technology*, 8 : 794–826, 1979.

Derwent Publications Ltd., London, , , : J,A, 0012037 (Pentel KK), Jan. 29, 1977. (Abstract).

"Photo–bleachable dyes and, processes", *Research Disclosure*, : 85–87, 1975.

Jenkins, P.W. et al., "Photobleachable dye material", *Research Disclosure*, : 18 [No. 12932], 1975.

Lamberts, R.L., "Recording color grid patterns with lenticules", *Research Disclosure*, : 18–19 [No. 12923], 1975.

Karmanova, L.S. et al., "Light stabilizers of daytime fluorescent paints", *Chemical Abstracts*, 82 : 147 [No. 59971p], 1975.

Prokopovich, B. et al., "Selection of effective photoinducers for rapid hardening of polyester varnish PE–250", *Chemical Abstracts*, 83 : 131 [No. 81334a], 1975.

"Variable Contrast Printing System", *Research Disclosure*, : 19 [No. 12931], 1975.

Chang, I.F., et al., "Color Modulated Dye Ink Jet Printer", *IBM Technical Disclosure Bulletin*, 17(5: 1520–1521), 1974.

"Darocur 1173: Liquid Photoiniator, , : for Ultraviolet Curing of Coatings", 1974.

Fischer, , "Submicroscopic contact imaging, , : with visible light by energy transfer".

Rigdon, J.E., "In Search of Paper that Spies Can't Copy", *Wall Street Journal*, :.

Chatterjee,S. et al., Photochemistry of Carbocyanine Alkyltriphenylborate Salts: Intra–Ion–Pair Electron Transfer and, *J. Am. Chem. Soc.*, 112 : 6329–6338.

"Assay—Physical and Chemical Analysis of Complexes", *AMAIZO*, :.

"Cyclodextrin", *AMAIZO*, :.

"Beta Cyclodextrin Polymer (BCDP)", *AMAIZO*, :.

"Chemically Modified Cyclodextrins", *AMAIZO*, :.

"Cyclodextrin Complexation", *American Maize Products Co.*, :.

"Cyclodextrins: A Breakthrough for Molecular Encapsulation", *American Maize Products Co. (AMAIZO)*:.

"Monomers", *Scientific Polymer Products Inc.*, :.

Suppan, Paul, "Quenching of Excited States", *Chemistry and Light*,: 65–69.

Yamaguchi, H. et al., "Supersensitization. Aromatic ketones as supersensitizers", *Chemical Abstracts*, 53 : 107 (d).

Stecher, H., "Ultraviolet–absorptive additives in adhesives, lacquers and plastics", *Chemical Abstracts*, 53 : 14579 (c).

Maslennikov, A.S., "Coupling of diazonium salts with ketones", *Chemical Abstracts*, 60 : 3128e.

Derwent Publications, Ltd., London, , : SU 292698–S Jan. 15, 1971 (abstract).

Derwent Publication, Ltd., London, , , : JA 7226653.

Derwent Publications Ltd., London, , , : 2416259.

Derwent Publications Ltd., London, , , : 4 9128022.

Derwent Publications Ltd., London, , , : 47 45409.

Derwent Publications, Ltd., London, , , : 7112489.

Derwent Publications, Ltd., London, , , : J6 2270665 (Konishiroku Photo KK), Nov. 25, 1987 (Abstract).

Derwent Publications, Ltd., London, , , : EP 0280653, Aug. 31, 1988 (Abstract).

Derwent Publications, Ltd., London, , , : SU 1423656 (Kherson Ind Inst), Sep. 15, 1988 (Abstract).

Abstract of Patent, JP 405195450, . :.

Derwent Publications, Ltd., London, , , : J6 1041381 (Osaka Prefecture), Feb. 27, 1986 (Abstract).

Derwent Publications, Ltd., London, , , : JA 0061785 (Nippon Senka KK), Apr. 14, 1982 (Abstract).

Derwent Publications, Ltd., London, , , : EP 0072775 (Ciba Geigy AG), Feb. 23, 1983 (Abstract).

Derwent Publications, Ltd., London, , , : J6 3108074 (Konishiroku Photo KK), May 12, 1988 (abstract).

Derwent Publications, Ltd., . . : London,J6 3108073 (Konishiroku Photo KK), May 12, 1988 (Abstract).

Derwent Publications, Ltd., London, . . : J6 3112770 (Toray Ind Inc), May 17, 1988 (Abstract).

Derwent Publications, Ltd., London, , , : JP 403269167 (Japan Wool Textile KK), Nov. 29, 1991 (Abstract).

Gafney et al., Photochemical Reactions of Copper (II) –1,3–Diketonate Complexes, *Journal of the Americqual,: Chemical Society*.

Gross et al., Laser direct–write metallization in thin palladium acetate films, *J. App. Phys.*, 61 : 1628–1632 (4).

Al–Ismail et al., Some experimental results on thin polypropylene films loaded with finely–dispersed copper, *Journal of Materials Science*, : 415–418.

Baufay et al., Optical self–regulation during laser–induced oxidation of copper, *J. Appl. Phys*, 61 : 4640–4651 9).

Esrom et al., Large area Photochemical Dry Etching of Polymers iwth Incoherent Excimer UV Radiation, *MRS Materials Research Society*, : 1–7.

Derwent Publications, Ltd., London, , : CA, 1086–719, (Sherwood Medical) Sep. 3, 1980 (Abstract).

New Excimer UV Sources for Industrial Applications, *ABB Review*, 391 : 1–10.

Kogelschatz, Silent–discharge driven excimer UV sources and their applications, *Applied Surface Science*, : 410–423.

Eliasson et al., New Trends in High Intensity UV Generation, *EPA Newsletter*, (32) : 29–40.

Esrom et al., Excimer Laser–Induced Decomposition of Aluminum Nitride, *Materials Research Society Fall Meeting*, : 1–6.

Esrom et al., Investrigatin of the mechanism of the UV–induced palladium depositions processf from thin solid, *Applied Surface Science*, 46 : 158–162.

Kogelschatz et al., New Incoherent Ultraviolet Excimer, , : Sources for Photolytic Material Deposition.

Esrom et al., Metal deposition with a windowless VUV excimer source, *Applied Surface Science*,: 1–5.

Esrom et al., UV excimer laser–induced pre–nucleation of surfaces followed by electroless metallization, *Chemtronics*, 4 : 216–223.

Esrom, Excimer Laser–Induced Surface Activation of Aln for Electroless Metal Deposition, *Mat. Res. Sco.lSymp. Proc.*, 204 : 457–465.

Zhang et al., UV–induced decompositin of adsorbed Cu–acetylacetonate films at room temperature for electroless, *Applied Surface Science*, : 1–6.

Esrom et al., VUV light–induced deposition of palladium using an incoherent Xe2* excimer source, *Chemtronics*, 4:.

Lakshman, Electronic Absorption Spectrum of Copper Formate Tetrahydrate , *Chemical Physics Letters*, 31 : 331–334 (2).

Esrom et al., UV Light–Induced Deposition of Copper Films, , : C5–719 –C5–725.

Esrom et al., Metal Deposition with Incoherent Excimer Radiation, *mat. Res. Soc. Symp. Proc.*, 158 : 189–198.

Zhang et al., VUV synchrotron radiation processing of thin palladium acetate spin–on films for metallic surface, *Applied Surface Science*, 46 : 153–157.

Esrom, UV Excimer Laer–Induced Deposition of Palladium from palladiym Acetate Films, *Mat. Res. Soc. Symp. Proc.*, 158 : 109–117.

German company develops reuseable paper, *Pulp & Paper*, :.

Derwent Publications, Ltd., London, , : J6 0011–449–A (Taoka Chemical KK) Jan. 21, 1985 (abstract).

Derwent Publications, Ltd., London, , : J5 7139–146 (Showa Kako KK) Aug. 27, 1982(abstract).

Derwent Publications, Ltd., London, , : J4 9131–226 (TNational Cash Register C) Dec. 16, 1974 (abstract).

Derwent Publications, Ltd., London, , : CA 1086–719 (Sherwood Medical) Sep. 30, 1980 (abstract).

PHOTOREACTOR COMPOSITION CONTAINING AN ARYLKETOALKENE WAVELENGTH-SPECIFIC SENSITIZER

TECHNICAL FIELD

The present invention relates to a composition and method for generating a reactive species. The present invention more particularly relates to a composition and method for generating reactive species which can be used to polymerize or photocure polymerizable unsaturated material.

BACKGROUND OF THE INVENTION

The present invention relates to a method of generating a reactive species. The present invention also relates to radiation-initiated polymerization and curing processes. For convenience, much of the discussion which follows centers on free radicals as a particularly significant reactive species. Such discussion, however, is not to be construed as limiting either the spirit or scope of the present invention.

Polymers long have served essential needs in society. For many years, these needs were filled by natural polymers. More recently, synthetic polymers have played an increasingly greater role, particularly since the beginning of the 20th century. Especially useful polymers are those prepared by an addition polymerization mechanism, i.e., free radical chain polymerization of unsaturated monomers, and include, by way of example only, coatings and adhesives. In fact, the majority of commercially significant processes is based on free-radical chemistry. That is, chain polymerization is initiated by a reactive species which often is a free radical. The source of the free radicals is termed an initiator or photoinitiator.

Improvements in free radical chain polymerization have focused both on the polymer being produced and the photoinitiator. Whether a particular unsaturated monomer can be converted to a polymer requires structural, thermodynamic, and kinetic feasibility. Even when all three exist, kinetic feasibility is achieved in many cases only with a specific type of photoinitiator. Moreover, the photoinitiator can have a significant effect on reaction rate which, in turn, may determine the commercial success or failure of a particular polymerization process or product.

A free radical-generating photoinitiator may generate free radicals in several different ways. For example, the thermal, homolytic dissociation of an initiator typically directly yields two free radicals per initiator molecule. A photoinitiator, i.e., an initiator which absorbs light energy, may produce free radicals by either of two pathways:

(1) the photoinitiator undergoes excitation by energy absorption with subsequent decomposition into one or more radicals; or (2) the photoinitiator undergoes excitation and the excited species interacts with a second compound (by either energy transfer or a redox reaction) to form free radicals from the latter and/or former compound(s).

While any free radical chain polymerization process should avoid the presence of species which may prematurely terminate the polymerization reaction, prior photoinitiators present special problems. For example, absorption of the light by the reaction medium may limit the amount of energy available for absorption by the photoinitiator. Also, the often competitive and complex kinetics involved may have an adverse effect on the reaction rate. Moreover, commercially available radiation sources, such as medium and high pressure mercury and xenon lamps, emit over a wide wavelength range, thus producing individual emission bands of relatively low intensity. Most photoinitiators only absorb over a small portion of the emission spectra and, as a consequence, most of the lamps' radiation remains unused. In addition, most known photoinitiators have only moderate quantum yields (generally less than 0.4) at these wavelengths, indicating that the conversion of light radiation to radical formation can be more efficient.

Thus, there are continuing opportunities for improvements in free radical polymerization photoinitiators.

SUMMARY OF THE INVENTION

The present invention addresses some of the difficulties and problems discussed above by the discovery of an efficient composition and method for utilizing radiation. Hence, the present invention comprehends a composition and method for generating a reactive species which includes providing a wavelength-specific sensitizer in association with a reactive species-generating photoinitiator and irradiating the wavelength-specific sensitizer.

The association of a wavelength-specific sensitizer with a reactive species-generating photoinitiator results in a structure referred to herein for convenience as a photoreactor composition. One major advantage of the wavelength-specific sensitizers which make up the present invention is that they efficiently absorb radiation at wavelengths between approximately 250 nm and 350 nm.

The present method involves effectively tuning the energy-absorbing entity, referred to herein as a photoreactor composition, to efficiently utilize an emitted band of radiation. The wavelength-specific sensitizer effectively absorbs photons and efficiently transfers the absorbed energy to the photoinitiator which, in turn, generates a reactive species. The wavelength-specific sensitizer is adapted to have an absorption peak generally corresponding to a maximum emission band of the radiation source.

As a result of the wavelength-specific sensitizer of the present invention absorbing radiation in the range of about 250 to 350 nanometers, the photoreactor composition of the present invention will generate one or more reactive species upon exposure to sunlight. Accordingly, the photoreactor composition of the present invention provides a method for the generation of reactive species that does not require the presence of a particular light source.

The present invention also includes a method of polymerizing an unsaturated monomer by exposing the unsaturated monomer to radiation in the presence of the efficacious photoreactor composition described above. When an unsaturated oligomer/monomer mixture is employed in place of the unsaturated monomer, curing is accomplished.

The present invention further includes a film and a method for producing a film, by drawing an admixture of unsaturated polymerizable material and the photoreactor composition of the present invention, into a film and irradiating the film with an amount of radiation sufficient to polymerize the composition. When the unsaturated polymerizable material is an unsaturated oligomer/monomer mixture, curing is accomplished. The admixture may be drawn into a film on a nonwoven web or on a fiber, thereby providing a polymer-coated nonwoven web or fiber, and a method for producing the same.

The present invention also includes an adhesive composition comprising an unsaturated polymerizable material admixed with the photoreactor composition of the present invention. Similarly, the present invention includes a laminated structure comprising at least two layers bonded together with the above described adhesive composition, in which at least one layer is a cellulosic or polyolefin nonwoven web or film. Accordingly, the present invention provides a method of laminating a structure wherein a structure having at least two layers with the above described adhesive composition between the layers is irradiated to polymerize the adhesive composition. When the unsaturated polymerizable material in the adhesive is an unsaturated oligomer/monomer mixture, the adhesive is irradiated to cure the composition.

DETAILED DESCRIPTION OF THE INVENTION

Figure 1:
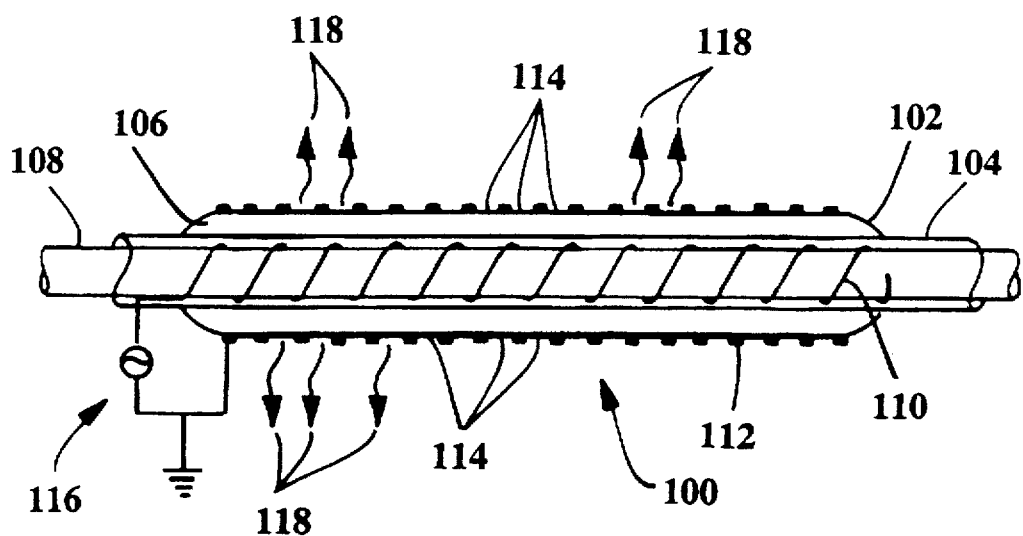
FIG. 1 is a diagrammatic representation of the excimer lamp employed in the examples.

The present invention is directed to the unexpected discovery of an efficient reactive species-generating composition and methods for utilizing the same. More particularly, the present invention includes a composition and method for generating a reactive species which includes providing a wavelength-specific sensitizer in association with a reactive species-generating photoinitiator and irradiating the wavelength-specific sensitizer. The association of a wavelength-specific sensitizer with a reactive species-generating photoinitiator results in a structure referred to herein for convenience as a photoreactor composition.

The present invention also comprehends a method of polymerizing an unsaturated polymerizable material by exposing the unsaturated material to radiation in the presence of the efficacious photoreactor composition described above. Further, the present invention includes a film and a method for producing a film, by drawing an admixture of unsaturated polymerizable material and the photoreactor composition of the present invention, into a film and irradiating the film with an amount of radiation sufficient to polymerize the composition.

Also, the present invention includes an adhesive composition comprising an unsaturated polymerizable material admixed with the photoreactor composition of the present invention. Similarly, the present invention includes a laminated structure comprising at least two layers bonded together with the above described adhesive composition, in which at least one layer is a cellulosic or polyolefin nonwoven web or film. Accordingly, the present invention provides a method of laminating a structure wherein a structure having at least two layers with the above described adhesive composition between the layers is irradiated to polymerize the adhesive composition.

The photoreactor composition of the present invention will be described in detail below, followed by a detailed description of the method of generating reactive species, and the various representative applications of the method.

The photoreactor composition of the present invention is the wavelength-specific sensitizer associated with a reactive species-generating photoinitiator. Accordingly, the term "photoreactor composition" is used herein to mean a wavelength-specific sensitizer associated with a reactive species-generating photoinitiator. In an embodiment where the sensitizer is admixed with the photoinitiator, the term "photoreactor composition" is used to mean the admixture. In the embodiment where the sensitizer is covalently bonded to the photoinitiator, the term "photoreactor composition" is used to mean the resultant molecule.

The term "associated" as used herein is meant to include any means which results in the wavelength-specific sensitizer and the reactive species-generating photoinitiator being in sufficiently close proximity to each other to permit the transfer of energy absorbed by the sensitizer to the photoinitiator. For example, the wavelength-specific sensitizer and the reactive species-generating photoinitiator may be bonded to each other or to a spacer molecule as described hereinafter by covalent, hydrogen, van der Waals, or ionic bonds. Alternatively, the sensitizer and the photoinitiator may be physically admixed.

The term "wavelength-specific sensitizer" is used herein to mean that the sensitizer is adapted to have an absorption wavelength band generally corresponding to an emission peak of the radiation. Either or both of the sensitizer and the radiation may have more than one absorption wavelength band and emission peak, respectively. In the event both the sensitizer and the radiation have more than one absorption wavelength band and emission peak, respectively, the general correspondence just described need not be limited to a single absorption wavelength band and a single emission peak.

According to the present invention, the "wavelength-specific sensitizer" is an arylketoalkene wavelength-specific sensitizer having the following general formula:

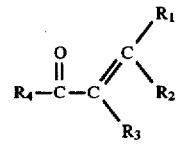

wherein $R_1$ is hydrogen, an alkyl, alkenyl, cycloalkyl, heterocycloalkyl, aryl or a heteroaryl group;

$R_2$ is hydrogen, alkyl, alkenyl, cycloalkyl, heterocycloalkyl, aryl or a heteroaryl group;

$R_3$ is hydrogen, alkyl, alkenyl, cycloalkyl, heterocycloalkyl, aryl or a heteroaryl group; and $R_4$ is an aryl, heteroaryl, or substituted aryl group.

Desirably, the arylketoalkene sensitizer has the following formula:

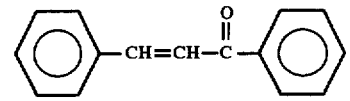

which efficiently absorbs radiation having a wavelength at about 308 nanometers, or

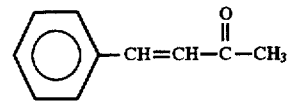

which efficiently absorbs radiation having a wavelength at about 280 nanometers. Desirably, the sensitizer of the present invention is in the trans configuration with respect to the double bond. However, the sensitizer may also be in the cis configuration across the double bond.

As stated above, the wavelength-specific sensitizer of the present invention may optionally be covalently bonded to the reactive species-generating photoinitiator. In that embodiment, the aryl group of the wavelength-specific sensitizer of the present invention can contain a group including, but not limited to, a carboxylic acid group, an aldehyde group, an amino group, a haloalkyl group, a hydroxyl group, or a thioalkyl group attached thereto to allow the arylketoalkene to be covalently bonded to the other molecule. Accordingly, the arylketoalkene sensitizer compound includes the following:

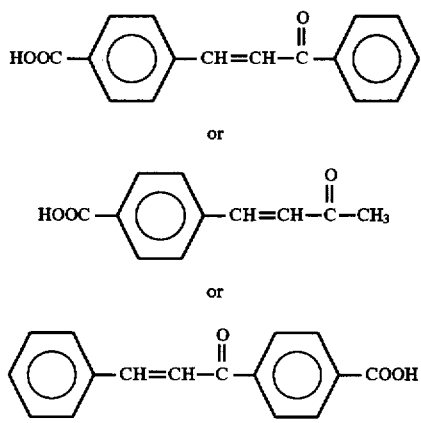

Although it is preferred that the group attached to the aryl group is para to the remainder of the sensitizer molecule, the group may also be ortho or meta to the remainder of the molecule.

The term "reactive species" is used herein to mean any chemically reactive species including, but not limited to, free-radicals, cations, anions, nitrenes, and carbenes. Illustrated below are examples of several of such species. Examples of carbenes include, for example, methylene or carbene, dichlorocarbene, diphenylcarbene, alkylcarbonylcarbenes, siloxycarbenes, and dicarbenes. Examples of nitrenes include, also by way of example, nitrene, alkyl nitrenes, and aryl nitrenes. Cations (sometimes referred to as carbocations or carbonium ions) include, by way of illustration, primary, secondary, and tertiary alkyl carbocations, such as methyl cation, ethyl cation, propyl cation, t-butyl cation, t-pentyl cation, t-hexyl cation; allylic cations; benzylic cations; aryl cations, such as triphenyl cation; cyclopropylmethyl cations; methoxymethyl cation; triarylsulphonium cations; and acyl cations. Cations also include those formed from various metal salts, such as tetra-n-butylammonium tetrahaloaurate(III) salts; sodium tetrachloroaurate(III); vanadium tetrachloride; and silver, copper(I) and (II), and thallium(I) triflates. Examples of anions (sometimes referred to as carbanions) include, by way of example, alkyl anions, such as ethyl anion, n-propyl anion, isobutyl anion, and neopentyl anion; cycloalkyl anions, such as cyclopropyl anion, cyclobutyl anion, and cyclopentyl anion; allylic anions; benzylic anions; aryl cations; and sulfur- or phosphorus-containing alkyl anions. Finally, examples of organometallic photoinitiators include titanocenes, fluorinated diaryltitanocenes, iron arene complexes, manganese decacarbonyl, and methylcyclopentadienyl manganese tricarbonyl. Organometallic photoinitiators generally produce free radicals or cations.

Any reactive species-generating photoinitiator may be used which generates the desired reactive species. With regard to the free radical-generating photoinitiators, these photoinitiators may be any of the photoinitiators known to those having ordinary skill in the art. The largest group of photoinitiators are carbonyl compounds, such as ketones, especially α-aromatic ketones. Examples of α-aromatic ketone photoinitiators include, by way of illustration only, benzophenones; xanthones and thioxanthones; α-ketocoumarins; benzils; α-alkoxydeoxybenzoins; benzil ketals or α,α-dialkoxydeoxybenzoins; enzoyldialkylphosphonates; acetophenones, such as α-hydroxycyclohexyl phenyl ketone, α,α-dimethyl-α-hydroxyacetophenone, α,α-dimethyl-α-morpholino-4-methylthio-acetophenone, α-ethyl-α-benzyl-α-dimethylaminoacetophenone, α-ethyl-α-benzyl-α-dimethylamino-4-morpholinoacetophenone, α-ethyl-α-benzyl-α-dimethylamino-3, 4dimethoxyacetophenone, α-ethyl-α-benzyl-α-dimethylamino-4-methoxyacetophenone, 60 -ethyl-α-benzyl-α-dimethylamino-4-dimethylaminoacetophenone, α-ethyl-α-benzyl-α-dimethylamino-4-methylacetophenone, α-ethyl-α-(2-propenyl)-α-dimethylamino-4-morpholinoacetophenone,α,α-bis(2-propenyl)-α-dimethylamino- 4-morpholinoacetophenone, α-methyl-α-benzyl-α-dimethylamino-4-morpholinoacetophenone, and α-methyl-α-(2-propenyl)-α-dimethylamino-4-morpholinoaceto-phenone; α,α-dialkoxyaceto-phenones; α-hydroxyalkylphenones; O-acyl α-oximino ketones; acylphosphine oxides; fluorenones, such as fluorenone, 2-t-butylperoxycarbonyl-9-fluorenone, 4-t-butylperoxycarbonyl-nitro-9-fluorenone, and 2,7-di-t-butylperoxy-carbonyl-9-fluorenone; and α- and β-naphthyl carbonyl compounds. Other free radical generating photoinitiators include, by way of illustration, triarylsilyl peroxides, such as triarylsilyl t-butyl peroxides; acylsilanes; and some organometallic compounds. The free radical-generating initiator desirably will be an acetophenone.

The types of reactions that various reactive species enter into include, but are not limited to, addition reactions, including polymerization reactions; abstraction reactions; rearrangement reactions; elimination reactions, including decarboxylation reactions; oxidation-reduction (redox) reactions; substitution reactions; and conjugation/deconjugation reactions.

In the embodiment where the wavelength-specific sensitizer is bound to the reactive species-generating photoinitiator, any suitable method that is known in the art may be used to bond the sensitizer to the photoinitiator. The choice of such method will depend on the functional groups present in the sensitizer and photoinitiator and is readily made by those having ordinary skill in the art. Such bonding may be accomplished by means of functional groups already present in the molecules to be bonded, by converting one or more functional groups to other functional groups, by attaching functional groups to the molecules, or through one or more spacer molecules.

Examples 1–3 herein describe methods of preparing the arylketoalkene sensitizer of the present invention, and covalently bonding it to a photoinitiator, namely DAROCUR 2959. The reaction described in Example 3 may be used on any arylketoalkene sensitizer of the present invention having a carboxylic acid functional group on $R_1$ or $R_2$, whichever is the aryl group. This reaction of any arylketoalkene sensitizer is represented by the formula below, wherein $R_3$ represents the remainder of the arylketoalkene sensitizer of the present invention, and wherein the carboxylic acid group is attached to $R_1$ or $R_2$:

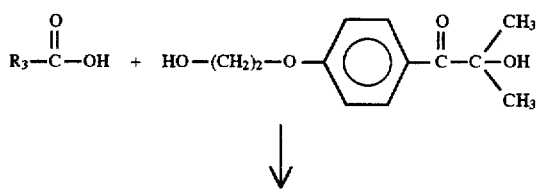

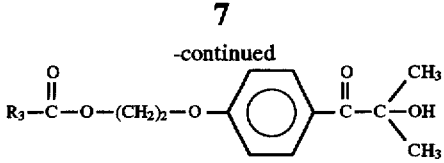

Desirably, the photoreactor composition of the present invention is represented by the following formula:

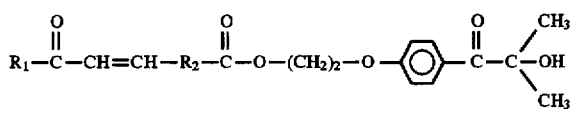

More desirably, the photoreactor composition of the present invention is represented by the following formulas:

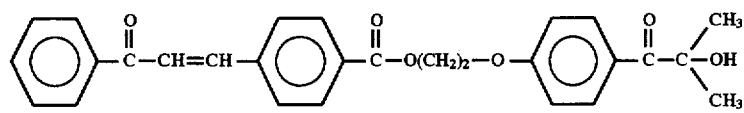

or

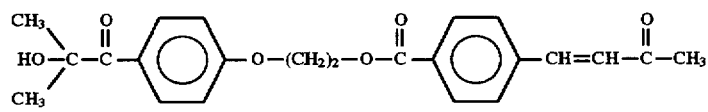

It is to be understood that the above reaction is merely one method of binding the sensitizer of the present invention to a photoinitiator, and that other methods known in the art may be used.

The term "spacer molecule" is used herein to mean any molecule which aids in the bonding process. For example, a spacer molecule may assist in the bonding reaction by relieving steric hindrance. Alternatively, a spacer molecule may allow use of more reactive or more appropriate functional groups, depending upon the functional groups present in the sensitizer and photoinitiator. It is contemplated that a spacer molecule may aid in the transfer of energy from the sensitizer to the photoinitiator, by either allowing a more favorable conformation or providing a more favorable energy transfer pathway.

As noted earlier, the wavelength-specific sensitizer is adapted to have an absorption wavelength band generally corresponding to an emission peak of the radiation. In addition, the wavelength-specific sensitizer will have a high intensity of absorption. For example, the wavelength-specific sensitizer may have a molar extinction coefficient greater than about 5,000 liters per mole per cm (1 mole$^{-1}$ cm$^{-1}$) at an absorption maximum. As another example, the wavelength-specific sensitizer may have a molar extinction coefficient (absorptivity) greater than about 10,000 1 mole$^{-1}$ cm$^{-1}$. As a further example, the wavelength-specific sensitizer will have a molar extinction coefficient greater than about 20,000 1 mole$^{-1}$ cm$^{-1}$.

The absorption characteristics of the wavelength-specific sensitizer are not limited to a single wavelength band. Many compounds exhibit more than one absorption wavelength band. Consequently, a wavelength-specific sensitizer may be adapted to absorb two or more wavelength bands of radiation. Alternatively, two or more wavelength-specific sensitizers may be associated with a reactive species-generating photoinitiator. Such two or more wavelength-specific sensitizers may absorb the same wavelength band or they may absorb two or more different wavelength bands of radiation.

The method of the present invention involves generating a reactive species by exposing a photoreactor composition to radiation in which the photoreactor composition includes a wavelength-specific sensitizer associated with a reactive species-generating photoinitiator. In other words, the method involves providing a wavelength-specific sensitizer in association with a reactive species-generating photoinitiator and irradiating the wavelength-specific sensitizer.

The term "quantum yield" is used herein to indicate the efficiency of a photochemical process. More particularly quantum yield is a measure of the probability that a particular molecule will absorb a quantum of light during its interaction with a photon. The term expresses the number of photochemical events per photon absorbed. Thus, quantum yields may vary from zero (no absorption) to 1.

The sensitizer absorbs photons having a specific wavelength and transfers the absorbed energy to the photoinitiator which, in turn, generates a reactive species. However, the efficiency with which a reactive species is generated is significantly greater than that experienced with the reactive species-generating photoinitiator alone. For example, the photoreactor composition desirably will have a quantum yield greater than about 0.5. More desirably, the quantum yield of the photoreactor composition will be greater than about 0.6. Even more desirably, the quantum yield of the photoreactor composition will be greater than about 0.7. Still more desirably, the quantum yield of the photoreactor composition will be greater than about 0.8, with the most desirable quantum yield being greater than about 0.9.

The term "polymerization" is used herein to mean the combining, e.g. covalent bonding, of large numbers of smaller molecules, such as monomers, to form very large molecules, i.e., macromolecules or polymers. The monomers may be combined to form only linear macromolecules or they may be combined to form three-dimensional macromolecules, commonly referred to as crosslinked polymers.

As used herein, the term "curing" means the polymerization of functional oligomers and monomers, or even polymers, into a crosslinked polymer network. Thus, curing is the polymerization of unsaturated monomers or oligomers in the presence of crosslinking agents.

The terms "unsaturated monomer," "functional oligomer," and "crosslinking agent" are used herein with their usual meanings and are well understood by those having ordinary skill in the art. The singular form of each is intended to include both the singular and the plural, i.e., one or more of each respective material.

The term "unsaturated polymerizable material" is meant to include any unsaturated material capable of undergoing polymerization. The term encompasses unsaturated monomers, oligomers, and crosslinking agents. Again, the singular form of the term is intended to include both the singular and the plural.

Exposing the photoreactor composition to radiation results in the generation of a reactive species. Thus, the photoreactor composition may be employed in any situation where reactive species are required, such as for the polymerization of an unsaturated monomer and the curing of an unsaturated oligomer/monomer mixture. The unsaturated monomers and oligomers may be any of those known to one having ordinary skill in the art. In addition, the polymerization and curing media also may contain other materials as desired, such as pigments, extenders, amine synergists, and such other additives as are well known to those having ordinary skill in the art.

By way of illustration only, examples of unsaturated monomers and oligomers include ethylene; propylene; vinyl chloride; isobutylene; styrene; isoprene; acrylonitrile; acrylic acid; methacylic acid; ethyl acrylate; methyl methacrylate; vinyl acrylate; allyl methacrylate; tripropylene glycol diacrylate; trimethylol propane ethoxylate acrylate; epoxy acrylates, such as the reaction product of a bisphenol A epoxide with acrylic acid; polyester acrylates, such as the reaction product of acrylic acid with an adipic acid/hexanediol-based polyester; urethane acrylates, such as the reaction product of hydroxypropyl acrylate with diphenylmethane-4,4'-diisocyanate; and polybutadiene diacrylate oligomer.

Accordingly, the present invention also comprehends a method of polymerizing an unsaturated monomer by exposing the unsaturated monomer to radiation in the presence of the efficacious photoreactor composition described above. When an unsaturated oligomer/monomer mixture is employed in place of the unsaturated monomer, curing is accomplished. It is to be understood that the polymerizable material admixed with the photoreactor composition of the present invention is to be admixed by means known in the art, and that the mixture will be irradiated with an amount of radiation sufficient to polymerize the material. The amount of radiation sufficient to polymerize the material is readily determinable by one of ordinary skill in the art, and depends upon the identity and amount of photoreactor composition, the identity and amount of the polymerizable material, the intensity and wavelength of the radiation, and the duration of exposure to the radiation.

The present invention further includes a film and a method for producing a film, by drawing an admixture of unsaturated polymerizable material and the photoreactor composition of the present invention, into a film and irradiating the film with an amount of radiation sufficient to polymerize the composition. When the unsaturated polymerizable material is an unsaturated oligomer/monomer mixture, curing is accomplished. Any film thickness may be produced, as per the thickness of the admixture formed, so long as the admixture sufficiently polymerizes upon exposure to radiation. The admixture may be drawn into a film on a nonwoven web or on a fiber, thereby providing a polymer-coated nonwoven web or fiber, and a method for producing the same. Any method known in the art of drawing the admixture into a film may be used in the present invention. The amount of radiation sufficient to polymerize the material is readily determinable by one of ordinary skill in the art, and depends upon the identity and amount of photoreactor composition, the identity and amount of the polymerizable material, the thickness of the admixture, the intensity and wavelength of the radiation, and duration of exposure to the radiation.

The term "fiber" as used herein denotes a threadlike structure. The fibers used in the present invention may be any fibers known in the art. The term "nonwoven web" as used herein denotes a web-like matter comprised of one or more overlapping or interconnected fibers in a nonwoven manner. It is to be understood that any nonwoven fibers known in the art may be used in the present invention.

The present invention also includes an adhesive composition comprising an unsaturated polymerizable material admixed with the photoreactor composition of the present invention. Similarly, the present invention includes a laminated structure comprising at least two layers bonded together with the above described adhesive composition, in which at least one layer is a cellulosic or polyolefin nonwoven web or film. Accordingly, the present invention provides a method of laminating a structure wherein a structure having at least two layers with the above described adhesive composition between the layers is irradiated to polymerize the adhesive composition. When the unsaturated polymerizable material in the adhesive is an unsaturated oligomer/monomer mixture, the adhesive is irradiated to cure the composition.

It is to be understood that any layers may be used in the present invention, on the condition that at least one of the layers allows sufficient radiation to penetrate through the layer to enable the admixture to polymerize sufficiently. Accordingly, any cellulosic or polyolefin nonwoven web or film known in the art may be used as one of the layers so long as they allow radiation to pass through. Again, the amount of radiation sufficient to polymerize the admixture is readily determinable by one of ordinary skill in the art, and depends upon the identity and amount of photoreactor composition, the identity and amount of the polymerizable material, the thickness of the admixture, the identity and thickness of the layer, the intensity and wavelength of the radiation, and the duration of exposure to the radiation.

The radiation to which the photoreactor composition is exposed generally will have a wavelength of from about 4 to about 1,000 nanometers. Thus, the radiation may be ultraviolet radiation, including near ultraviolet and far or vacuum ultraviolet radiation; visible radiation; and near infrared radiation. Desirably, the radiation will have a wavelength of from about 100 to about 900 nanometers. More desirably, the radiation will have a wavelength of from about 100 to 700 nanometers.

Desirably, when the reactive species-generating photoinitiator is an organic compound, the radiation will be ultraviolet radiation having a wavelength of from about 4 to about 400 nanometers. More desirably, the radiation will have a wavelength of from about 100 to about 375 nanometers, and even more desirably will have a wavelength of from 200 to about 370 nanometers. For example, the radiation may have a wavelength of from about 222 to about 308 nanometers. The radiation desirably will be incoherent, pulsed ultraviolet radiation from a dielectric barrier discharge excimer lamp.

Excimers are unstable excited-state molecular complexes which occur only under extreme conditions, such as those temporarily existing in special types of gas discharge. Typical examples are the molecular bonds between two rare gaseous atoms or between a rare gas atom and a halogen atom. Excimer complexes dissociate within less than a microsecond and, while they are dissociating, release their binding energy in the form of ultraviolet radiation. The dielectric barrier excimers in general emit in the range of from about 125 nm to about 500 nm, depending upon the excimer gas mixture.

Dielectric barrier discharge excimer lamps (also referred to hereinafter as "excimer lamp") are described, for example, by U. Kogelschatz, "Silent discharges for the generation of ultraviolet and vacuum ultraviolet excimer radiation." Pure & Appl. Chem., 62, No. 9, pp. 1667 1674 (1990); and E. Eliasson and U. Kogelschatz, "UV Excimer Radiation from Dielectric-Barrier Discharges." Appl. Phys. B. 46, pp. 299-303 (1988). Excimer lamps were developed by ABB Infocom Ltd., Lenzburg, Switzerland, and at the present time are available from Heraeus Noblelight GmbH, Kleinostheim, Germany.

The excimer lamp emits incoherent, pulsed ultraviolet radiation. Such radiation has a relatively narrow bandwidth, i.e., the half width is of the order of approximately 5 to 100 nanometers. Desirably, the radiation will have a half width of the order of approximately 5 to 50 nanometers, and more desirably will have a half width of the order of 5 to 25 nanometers. Most desirably, the half width will be of the order of approximately 5 to 15 nanometers.

The ultraviolet radiation emitted from an excimer lamp can be emitted in a plurality of wavelengths, wherein one or more of the wavelengths within the band are emitted at a maximum intensity. Accordingly, a plot of the wavelengths in the band against the intensity for each wavelength in the band produces a bell curve. The "half width" of the range of ultraviolet radiation emitted by an excimer lamp is defined as the width of the bell curve at 50% of the maximum height of the bell curve.

The emitted radiation of an excimer lamp is incoherent and pulsed, the frequency of the pulses being dependent upon the frequency of the alternating current power supply which typically is in the range of from about 20 to about 300 kHz. An excimer lamp typically is identified or referred to by the wavelength at which the maximum intensity of the radiation occurs, which convention is followed throughout this specification and the claims. Thus, in comparison with most other commercially useful sources of ultraviolet radiation which typically emit over the entire ultraviolet spectrum and even into the visible region, excimer lamp radiation is essentially monochromatic.

As a result of the wavelength-specific sensitizer of the present invention absorbing radiation in the range of about 250 to about 350 nanometers, and more particularly at about 270 to 320 nanometers, the photoreactor composition of the present invention will generate one or more reactive species upon exposure to sunlight. Accordingly, the photoreactor composition of the present invention provides a method for the generation of reactive species that does not require the presence of a special light source. The photoreactor composition of the present invention enables the production of adhesive and coating compositions that consumers can apply to a desired object and polymerize or cure upon exposure to sunlight. The photoreactor composition of the present invention also enables numerous industry applications wherein unsaturated polymerizable materials may be polymerized merely upon exposure to sunlight. Therefore, the photoreactor composition of the present invention will eliminate the cost of purchasing and maintaining light sources in numerous industries wherein such light sources are necessary without the photoreactor composition of the present invention.

As shown in the Examples below, the superiority of the photoreactor compositions of the present invention over known photoinitiators is clear, even when the radiation is not the essentially monochromatic emission. The effective tuning of the photoreactor composition for a specific wavelength band permits the photoreactor composition to more efficiently utilize the target radiation in the emission spectrum of the radiating source corresponding to the "tuned" wavelength band, even though the intensity of such radiation may be much lower than, for example, radiation from a narrow band emitter, such as an excimer lamp. In other words, the effectiveness of the radiation transorber composition of the present invention is not necessarily dependent upon the availability or use of a narrow wavelength band radiation source.

Also, as shown in Example 4, the photoreactor composition of the present invention is exceptionally efficient. In Example 4, a mixture of Genomer 1500B with a concentration of only about 0.5% of the photoreactor composition produced in Example 3 was totally cured upon exposure to the excimer lamp. The concentration of photoreactor composition used in Example 4 is substantially lower than the amounts normally used in the prior art. Typical concentrations of conventional photoreactors in the prior art are between approximately 2% to 20% by weight.

The present invention is further described by the examples which follow. Such examples, however, are not to be construed as limiting in any way either the spirit or the scope of the present invention. In the examples, all parts are by weight, unless stated otherwise.

EXAMPLE 1

This example describes a method of synthesizing the following wavelength-specific sensitizer:

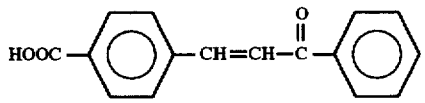

The wavelength-specific sensitizer is produced as summarized below:

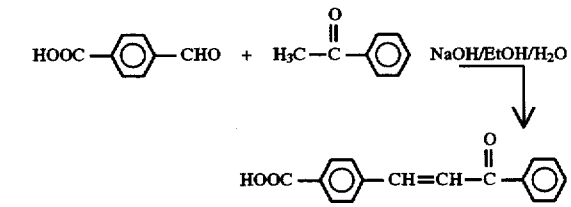

To a 250 ml round bottom flask fitted with a magnetic stir bar, and a condenser, was added 10.8 g (0.27 mole) sodium hydroxide (Aldrich), 98 g water and 50 g ethanol. The solution was stirred while being cooled to room temperature in an ice bath. To the stirred solution was added 25.8 g (0.21 mole) acetophenone (Aldrich) and then 32.2 g (0.21 mole) 4-carboxybenzaldehyde (Aldrich). The reaction mixture was stirred at room temperature for approximately 8 hours. The reaction mixture temperature was checked in order to prevent it from exceeding 30° C. Next, dilute HCl was added to bring the mixture to neutral pH as indicated by universal pH indicator paper. The white/yellow precipitate was filtered using a Buchner funnel to yield 40.0 g (75%) after drying on a rotary pump for four hours. The product was used below without further purification.

The resulting reaction product had the following physical parameters:

Mass. Spec. m/e (m$^+$) 252, 207, 179, 157, 105, 77, 51.

The ultraviolet radiation spectrum of the product had an extinction coefficient of about 24,000 at about 304 nanometers, and $\lambda_{max}$ was at 308 nanometers.

EXAMPLE 2

This example describes a method of making the following wavelength-selective sensitizer, namely 4-[4'-carboxy phenyl]-3-buten-2-one:

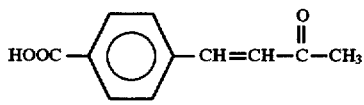

The wavelength-specific sensitizer was produced as summarized below:

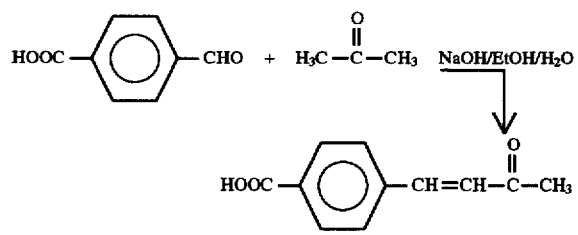

The method of Example 1 was followed except that acetone (Fisher, Optima Grade) was added first, and then the carboxybenzaldehyde was added. More particularly, 32.2 (0.21 mole) of carboxybenzaldehyde was reacted with 12.2 g (0.21 mole) of acetone in the sodium hydroxide/ethanol/ water mixture described in Example 1. Dilute HCl was added to bring the reaction mixture to neutral pH, yielding 37.1 g (91%) of a pale yellow powder which was used without further purification in the following examples.

The resulting reaction product, namely 4-[4'-carboxy phenyl]-3-buten-2-one, had the following physical parameters:

Mass. Spec. 190 (m$^+$), 175, 120.

EXAMPLE 3

This example describes a method of covalently bonding the compound produced in Example 1 to a photoinitiator, namely DAROCUR 2959, as is summarized below:

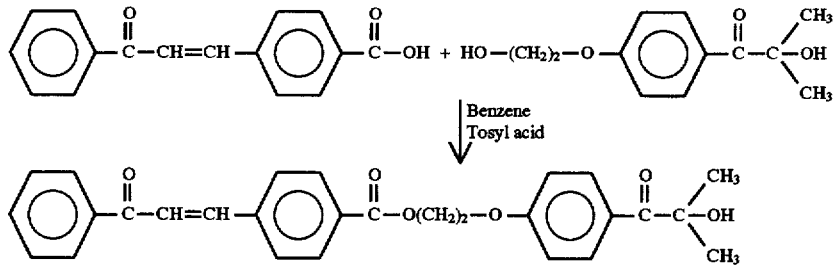

To a 500 ml round bottom flask fitted with a magnetic stir bar, and condensor, was placed 20 g (0.08 mole) of the composition prepared in Example 1, 17.8 g (0.08 mole) DAROCUR 2959 (Ciba-Geigy, N.Y.), 0.5 g p-toluenesulfonic acid (Aldrich), and 300 ml anhydrous benzene (Aldrich). The Dean and Stark adapter was put on the flask and the reaction heated at reflux for 8 hours after which point 1.5 ml of water had been collected (theo. 1.43 ml). The reaction mixture was then cooled and the solvent removed on a rotary evaporator to yield 35.4 g. The crude product was recrystallized from 30% ethyl acetate in hexane to yield 34.2 g (94%) of a white powder. The resulting reactor product had the following physical parameters:

Mass. Spectra: 458 (m$^+$), 440, 399, 322, 284.

EXAMPLE 4

The following experiment tested the curing ability of the compound produced in Example 3. More particularly, the compound produced in Example 3 was mixed with the difunctional alkyl urethane acrylate adhesive GENOMER® 1500B (Mader, Biddle Sawyer Corporation, New York, N.Y.) and exposed to a 308 nm excimer lamp on a conveyor belt. Two formulations were studied:

Formulation I

About 0.05 g of the compound produced in Example 3 was mixed with 10 g of (GENOMER® 1500B). Therefore the concentration of the compound produced in Example 3 in the mixture was about 0.5%. These components were mixed by means of a magnetic stirring bar at 80° C. A few drops of the mixture was placed on a heated metal plate (Q-Panel Company, Westlake, Ohio) and drawn down to a thickness of about 0.1 mm by means of a 0 draw-down bar (Industry Tech., Oldsmar, Fla.).

Formulation II

About 0.025 g of DAROCUR 2959 was mixed with 10 g of GENOMER 1500B. These components were mixed and then drawn out on heated metal plates with a 0 draw-down bar as per Formulation I.

Each plate was then exposed to a 308 nanometer excimer lamp on a conveyor belt for approximately 0.8 seconds. The conveyor belt was set at 50 feet/minute. The plate having Formulation I thereon was totally cured upon exposure to the excimer lamp. In contrast, the plate having Formulation II thereon remained tacky and was not fully cured.

EXAMPLE 5

This example describes the evaluation of the curing behavior of an adhesive containing the photoreactor compositions of Example 3 as reported in Example 4 upon exposure to ultraviolet radiation from an excimer lamp.

An excimer lamp configured substantially as described by Kozelschatz and Eliasson et al., supra, was employed and is shown diagrammatically in FIG. 1. With reference to FIG. 1, the excimer lamp 100 consisted of three coaxial quartz cylinders and two coaxial electrodes. The outer coaxial quartz cylinder 102 was fused at the ends thereof to a central coaxial quartz cylinder 104 to form an annular discharge space 106. An excimer-forming gas mixture was enclosed in the annular discharge space 106. An inner coaxial quartz cylinder 108 was placed within the central cylinder 104. The inner coaxial electrode 110 consisted of a wire wound around the inner cylinder 108. The outer coaxial electrode 112 consisted of a wire mesh having a plurality of openings 114. The inner coaxial electrode 110 and outer coaxial electrode 112 were connected to a high voltage generator 116. Electrical discharge was maintained by applying an alternating high voltage to the coaxial electrodes 110 and 112. The operating frequency was 40 kHz, the operating voltage 10 kV. Cooling water was passed through the inner coaxial quartz cylinder 108, thereby maintaining the temperature at the outer surface of the lamp at less than about 120° C. The resulting ultraviolet radiation was emitted through the openings 114 as shown by lines 118. The lamp was used as an assembly of four lamps 100 mounted side-by-side in a parallel arrangement.

A film of adhesive was deemed cured completely, i.e., through the entire thickness of the film, when it passed the scratch test; see, e.g., M. Braithwaite et al., "Chemistry & Technology of UV & EB Formulation for Coatings, Inks & Paints," Vol. IV, SITA Technology Ltd., London, 1991, pp. 11–12.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A photoreactor consisting of:

a reactive species-generating photoinitiator covalently bonded to a wavelength-specific sensitizer, the sensitizer being represented by one of the following formulae prior to bonding:

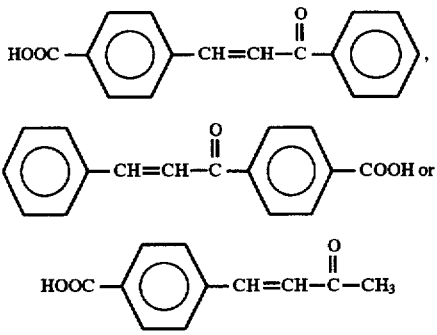

wherein the photoinitiator is covalently bonded through the carboxylic acid group of the sensitizer.

2. The photoreactor of claim 1, wherein the reactive species-generating photoinitiator generates a free radical, a carbene, a nitrene, an anion, or a cation.

3. A photoreactor having one of the following formulae:

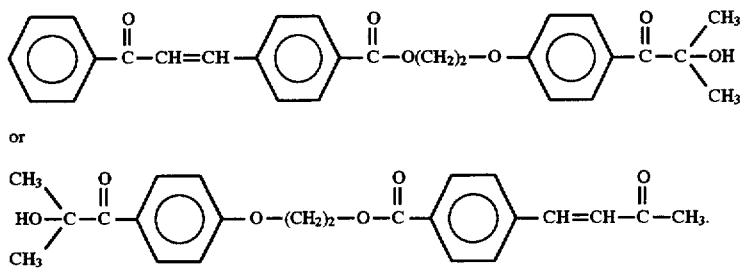

* * * * *